United States Patent [19]
Hambleton et al.

[11] Patent Number: 5,454,818
[45] Date of Patent: * Oct. 3, 1995

[54] INTRAOCULAR LENS FOLDER

[75] Inventors: Robert Hambleton, Plano; Stephen J. Van Noy, Fort Worth, both of Tex.

[73] Assignee: Alcon Laboratories, Inc., Fort Worth, Tex.

[*] Notice: The portion of the term of this patent subsequent to Mar. 1, 2011 has been disclaimed.

[21] Appl. No.: 280,268

[22] Filed: Jul. 26, 1994

Related U.S. Application Data

[63] Continuation-in-part of Ser. No. 4,357, Feb. 2, 1993, Pat. No. Des. 349,342.

[51] Int. Cl.⁶ .................................................. A61B 17/00
[52] U.S. Cl. ............................................................ 606/107
[58] Field of Search ...................... 606/1, 107, 205–211; D24/143; 623/4, 6; 206/5.1

[56] References Cited

U.S. PATENT DOCUMENTS

| D. 255,715 | 7/1980 | Markham . |
| 4,402,396 | 9/1983 | Graham . |
| 4,573,998 | 3/1986 | Mazzocco . |
| 4,619,657 | 10/1986 | Keates et al. . |
| 4,785,810 | 11/1988 | Baccala et al. ........................ 606/107 |
| 4,817,789 | 4/1989 | Paul . |
| 4,834,750 | 5/1989 | Gupta . |
| 4,844,065 | 7/1989 | Faulkner . |
| 4,844,093 | 7/1989 | Jampel et al. . |
| 4,844,242 | 7/1989 | Chen et al. . |
| 4,911,158 | 3/1990 | Weatherly . |
| 4,919,130 | 4/1990 | Stoy et al. . |
| 4,955,889 | 9/1990 | Van Gent . |
| 4,988,352 | 1/1991 | Poley . |
| 5,007,913 | 4/1991 | Dulebohn . |
| 5,066,297 | 11/1991 | Cumming . |
| 5,098,439 | 3/1992 | Hill et al. . |
| 5,100,410 | 3/1992 | Dulebohn . |
| 5,123,905 | 6/1992 | Kelman . |
| 5,133,737 | 7/1992 | Grismer ............................... 606/205 |
| 5,139,501 | 8/1992 | Klaas . |
| 5,171,241 | 12/1992 | Buboltz et al. . |
| 5,176,686 | 1/1993 | Poley . |
| 5,190,553 | 3/1993 | Kanert et al. . |
| 5,203,789 | 4/1993 | McDonald . |
| 5,203,790 | 4/1993 | McDonald . |
| 5,281,227 | 1/1994 | Sussman ............................... 606/107 |
| 5,290,293 | 3/1994 | Van Noy et al. ....................... 606/107 |

FOREIGN PATENT DOCUMENTS 2673526 10/1992 France .

Primary Examiner—Stephen C. Pellegrino
Assistant Examiner—Glenn Dawson
Attorney, Agent, or Firm—Jeffrey S. Schira

[57] ABSTRACT

An intraocular lens folder having a generally planar, open frame in the shape of a rounded "A" with a rimmed, open head at the top of the "A." The base of the "A" forms a pair of opposing legs or handles that join to form a hinge at the crotch where the handles attach to the head. The hinge allows the handles to be squeezed together and yet spring apart when released. Squeezing the handles causes the top edge of the head rim to compress and move toward the hinge. The open head contains a plurality of projections terminating in open, relieved jaws into which the IOL is placed. The location of the projections is such that when the handles are squeezed together and the rim moves toward the hinge, two of the jaws move toward each other, causing the IOL to be folded in half.

9 Claims, 3 Drawing Sheets

INTRAOCULAR LENS FOLDER

This application is a continuation-in-part application of Ser. No. 29/004,357, filed Feb. 2, 1993, now U.S. Pat. No. Des. 349,342.

BACKGROUND OF THE INVENTION

The present invention relates to intraocular lenses and particularly to foldable intraocular lenses.

For many years, the predominant method of treating a diseased lens is to remove the lens and replace it with an intraocular lens ("IOL"). Two surgical procedures are preferred for removing the diseased lens: extracapsular cataract extraction and phacoemulsification. Extracapsular cataract extraction involves removing the lens in a relatively intact condition by use of a vectus or similar surgical instrument. Phacoemulsification involves contacting the lens with the vibrating cutting tip of an ultrasonically driven surgical handpiece to emulsify the lens, thereby allowing the emulsified lens to be aspirated from the eye. Both surgical procedures require that the anterior lens capsule be cut to allow access to the lens itself and to allow the implantation of the replacement lens, and because the capsule bag is used to hold or retain the IOL in place after surgery, the opening should be as small as possible. Although extracapsular cataract extraction has been the preferred surgical technique, phacoemulsification is becoming increasingly popular, in part because of the relatively small (around 3 millimeters) tunnel incision that is used with phacoemulsification.

A typical IOL comprises an artificial lens ("optic") and at least one support member ("haptic") for positioning the IOL within the capsular bag. The diameter of the optic varies depending on the design of the IOL, but an optic diameter of around 5 millimeters (nun) to 6 mm is most common. When the surgical technique used is extracapsular cataract extraction, inserting the IOL through the relatively large incision presents no particular difficulties. However, when the surgical procedure used in phacoemulsification, the surgeon typically must widen the initial 3 mm tunnel incision enough to allow the IOL to be inserted into the capsular bag. Enlarging the incision reduces one of the advantages of phacoemulsification because of the possibility for postoperative complications associated with large incision ocular surgery, including induced astigmatism. Therefore, rollable or foldable IOL's have been developed that can be inserted into the capsular bag with minimal widening of the phacoemulsification incision.

As discussed in U.S. Pat. Nos. 4,573,998, 4,619,657, 4,834,750 and 4,919,130, the entire contents of which is incorporated herein in its entirety by reference, foldable IOL's generally are made from polyurethane elastomers, silicone elastomers, hydrogel polymer collagen compounds or organic or synthetic gel compounds. The lens is rolled, compressed or crushed by a special syringe or forceps and placed into the capsular bag without enlarging the incision. While these IOL's and insertion devices work well, the insertion devices are bulky and require practice to master their use.

A second generation of foldable IOL's have recently been introduced that are made from monomers derived from acrylacrylate or methacrylates and a crosslinking agent. Such monomers are described more fully in commonly assigned U.S. Pat. No. 5,290,892, the entire contents of which is incorporated by reference. Such materials are advantageous because they have higher refractive indices and, hence, allow the IOL to be thinner and fold more easily.

Prior to the present invention, to implant IOL's made from such acrylic materials, a special duckbill forceps with rounded jaws that will not close together completely (so as not to press the sides of the folded IOL together) was used. However, these forceps cannot, by themselves, fold the IOL, and the surgeon must hold the IOL with a second needle-nose or tying forceps while enveloping and folding the IOL with the duckbill forceps. This technique, while reliable, requires the use of two hands and a great deal of practice to master.

One IOL folder disclosed in U.S. Pat. No. 5,100,410 uses a pair of opposing jaws that when pressed together folds the IOL within a pair of duckbill forceps. However, the recessed jaws of the folder disclosed in this patent requires that the forceps be held in place on either side of the lens during folding operation, making it difficult for one person (such as the nurse) to fold the IOL while another person (such as the surgeon) holds the forceps.

Another IOL folder disclosed in U.S. Pat. No. 5,139,501 uses a base with a fixed jaw and an opposing, movable jaw. The IOL is placed between the jaws and the movable jaw is pressed toward the fixed jaw, thereby folding the soft IOL. However, this folder must be assembled from several pieces, increasing its manufacturing cost.

Accordingly, a need continues to exist for an inexpensive, one-handed device that will fold easily a soft IOL.

BRIEF SUMMARY OF THE INVENTION

The present invention improves upon prior art IOL folders by providing a plastic single piece folder that easily and reliably folds an IOL using only one hand and requires little practice to use properly. The device has a generally planar, open frame in the shape of a rounded "A" with a rimmed, open head at the top of the "A." The base of the "A" forms a pair of opposing legs or handles that join to form a hinge at the crotch where the handles attach to the head. The hinge allows the handles to be squeezed together and yet spring apart when released. Squeezing the handles causes the sides of the head to spread apart, thereby stretching the top edge of the head rim and pulling top edge downward toward the hinge. The open head contains a plurality of projections terminating in open, relieved jaws into which the IOL is placed. The location of the projections is such that when the handles are squeezed together and the rim moves toward the hinge, two of the jaws moves toward each other, causing the IOL to be folded in half. The folded IOL can then be grabbed easily by the insertion forceps. The folding operation is performed by the present invention entirely by squeezing the handles together and little practice or dexterity is required to perfect the folding technique. In addition, the folder of the present invention can also be used as a lens carrier and allows the lens to be rinsed and inspected by the surgeon without removing the lens from the folder.

Accordingly, one objective of the present invention is to provide a device for folding an intraocular lens.

Another objective of the present invention is to provide an intraocular lens folder that is easy to use.

Another objective of the present invention is to provide a single piece intraocular lens folder.

Still another objective of the present invention is to provide an intraocular lens folder that is inexpensive to manufacture.

A further objective of the present invention is to provide an intraocular lens folder that does not press the sides of the folder lens together.

Another objective of the present invention is to provide an intraocular lens folder that requires the use of only one hand to fold the lens.

Still another objective of the present invention is to provide an intraocular lens folder that also can be used as a lens carrier.

These and other and further objectives and advantages of the present invention will become apparent form the detailed description, drawings and claims that follow.

DETAILED DESCRIPTION OF THE INVENTION

Figure 1:
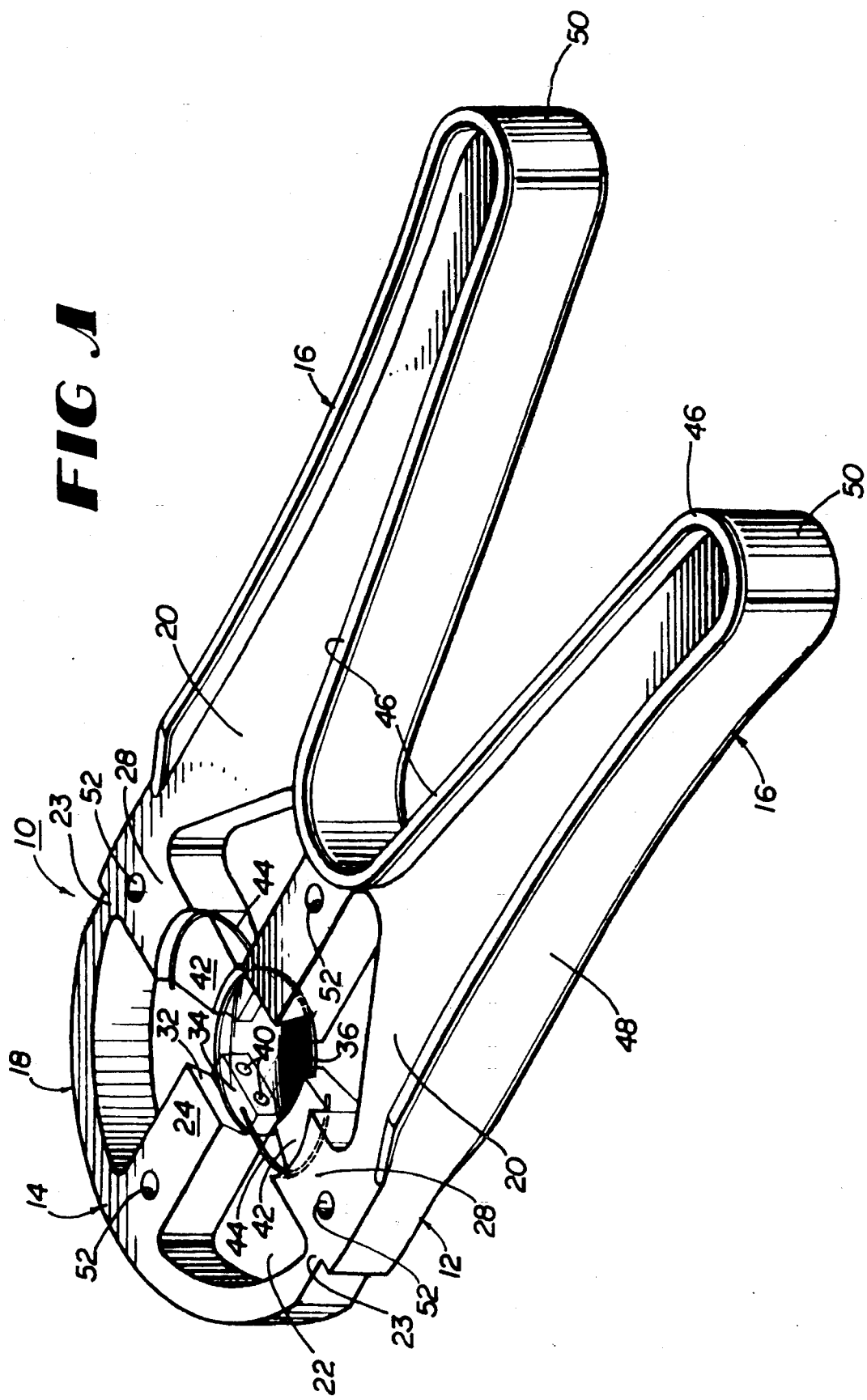
FIG. 1 is a perspective view of one embodiment of the intraocular lens folder of the present invention.
Figure 7:
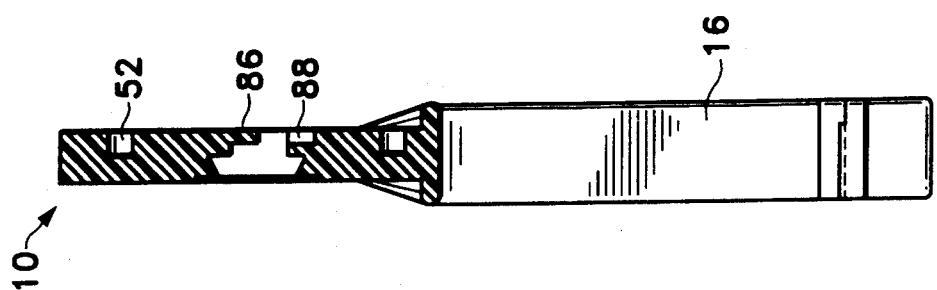
FIG. 7 is a cross-section view of the intraocular lens folder illustrated in FIG. 6 taken along line 7—7.
Figure 6:
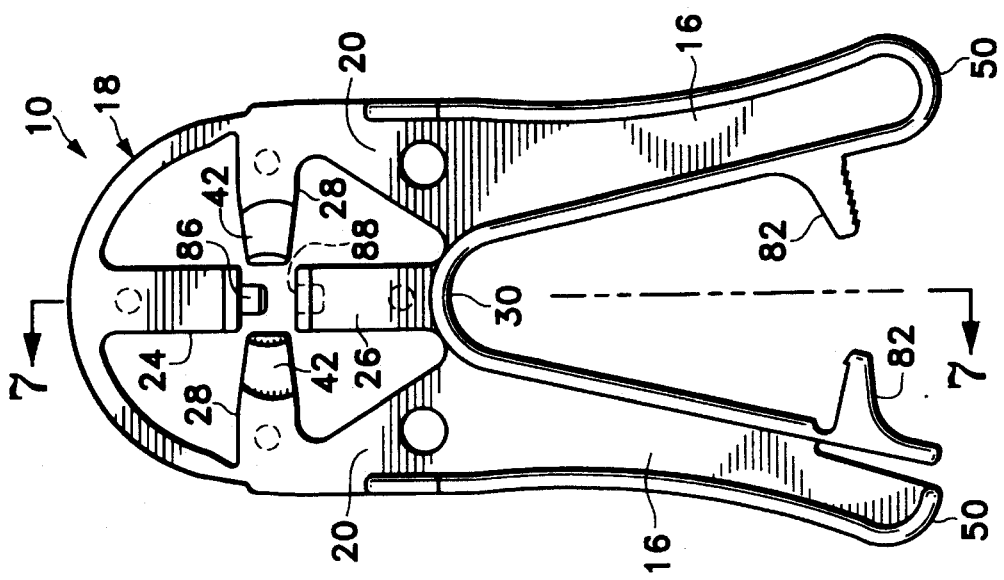
FIG. 6 is a top plan view of a second embodiment of the intraocular lens folder of the present invention.

As can be seen in FIG. 1, lens folder 10 of the present invention generally consists of frame 12 having a head 14 and handles 16. Frame 12 is preferably molded in one piece from a relatively soft plastic such as polypropylene or polyethylene. Head 14 generally is defined by a deformable, arcuate rim 18 and upper portions 20 so as to give head 14 a half ring-like appearance in plan view, as can best be seen in FIGS. 2 and 6. Projecting into hollow center 22 of head 14 are a plurality of opposing jaws 24, 26 and 28, jaw 24 being integrally formed in rim 18, jaws 28 being opposing and integrally formed in top portion 20 of handles 16 and jaw 26 being opposite jaw 24 and integrally formed in hinge 30 between handles 16. As best seen in FIGS. 1, 3, 4 and 5, jaws 24 and 26 contain clamping faces 32 that are undercut or relieved and contain a sill 34, thereby providing a stable platform for IOL 36 during shipment and storage and ensuring that IOL 36 will consistently fold in the correct direction. Jaw faces 32 may also contain pins 38 on either jaw 24 or jaw 26 that fit into holes 40 in either jaw 26 or jaw 24, respectively, when jaw 24 is forced into contact with jaw 26 as hereinafter described. Pins 38 and holes 40 ensure that jaws 24 and 26 remained aligned during contact. An alternative to the use of pins 38 and holes 40 includes using a tab 86 that fits into a corresponding slot 88 as shown in FIGS. 6 and 7. Jaws 24, 26 and 28 may also contains holes 52 that fit over pins (not shown) in an outer shipping container (not shown) and prevent folder 10 from moving within the shipping container. Jaws 28 may include a recess 42 into which haptics 44 of IOL 36 are placed to help hold IOL 36 in place during storage, shipping and folding.

Figure 2:
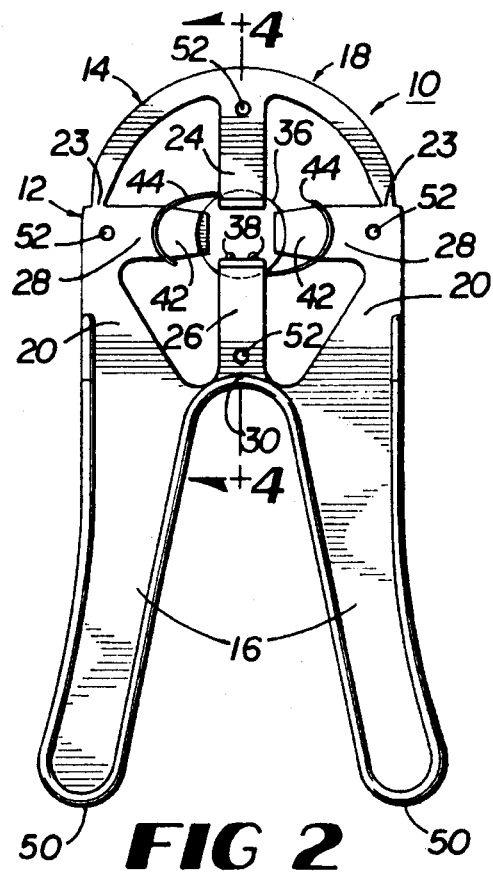
FIG. 2 is a top plan view of the intraocular lens folder illustrated in FIG. 1 shown in its relaxed state.
Figure 4:
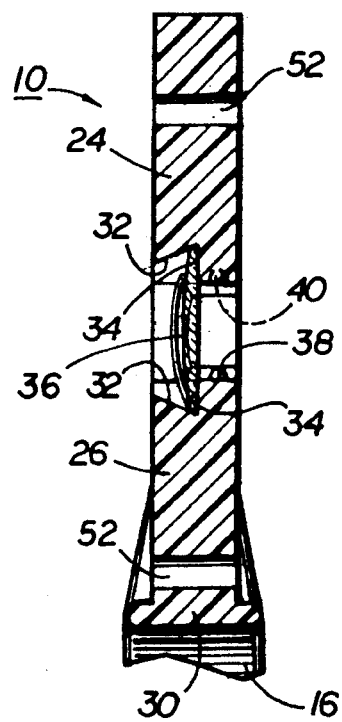
FIG. 4 is a cross-section view of the intraocular lens folder illustrated in FIG. 1 taken along line 4—4 in FIG. 2.
Figure 3:
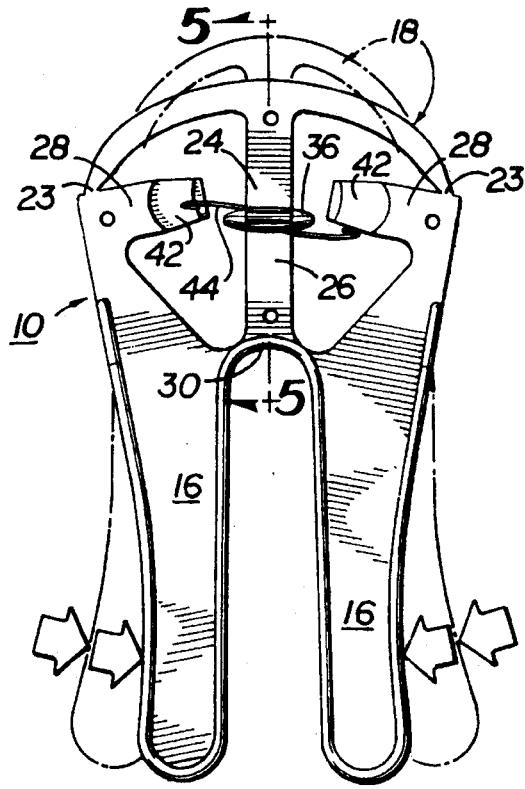
FIG. 3 is a top plan view of the intraocular lens folder similar to FIG. 2 but showing the folder in its flexed and deformed state.
Figure 5:
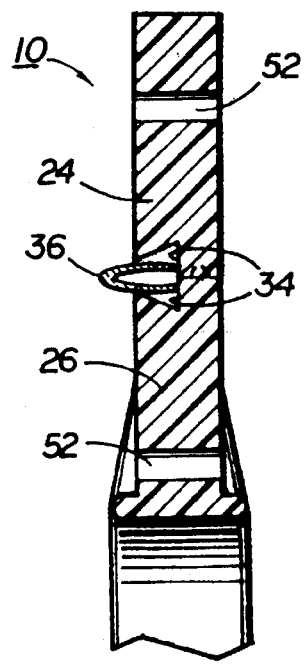
FIG. 5 is a cross-section view of the intraocular lens folder illustrated in FIG. 1 taken along line 5—5 in FIG. 3.

As can best be seen in FIGS. 1, 2 and 3, upper portion 20 of handles 16 merge with rim 18 at hinges 23 to form head 14. Handles 16 are connected at hinge 30 and extend outwardly from hinge 30 at a slightly divergent angle. Handles 16 may be of any cross-sectional shape but an "T" cross-section having stiffening ribs 46 is preferred.

In use, IOL 36 is placed within head 14 so that IOL 36 rests on sills 34 on jaw faces 32 and haptics 44 rest within recesses 42 on jaws 28, as illustrated in FIGS. 1 and 2. Force is applied to outer sides 48 of handles 16 so that handles 16 pivot toward each other about hinge 30. As terminal ends 50 of handles 16 rotate toward each other about hinge 30, upper portions 20 of handles 16 (which are on an opposite side of hinge 30 than ends 50) are drawn away from each other, as illustrated in FIG. 3. Pulling upper portions 20 of handles 16 away from each other causes jaws 28 to be pulled away from each other and also increases the radius of rim 18 at hinges 23, thereby flattening out rim 18. As rim 18 is flattened, jaw 24 is forced toward jaw 26. IOL 36, being captured between jaws 24 and 26 by relieved jaw faces 32, is forced to bend or fold outwardly or away from sills 34, thereby allowing IOL 36 to be removed easily from folder 10 in a folded configuration. To assist rim 18 in bending only at hinges 23, rim 18 may be of a rectangular shape (i.e., taller than it is thick). For example, rim 18 may be 0.25 inches tall.

Figure 8:
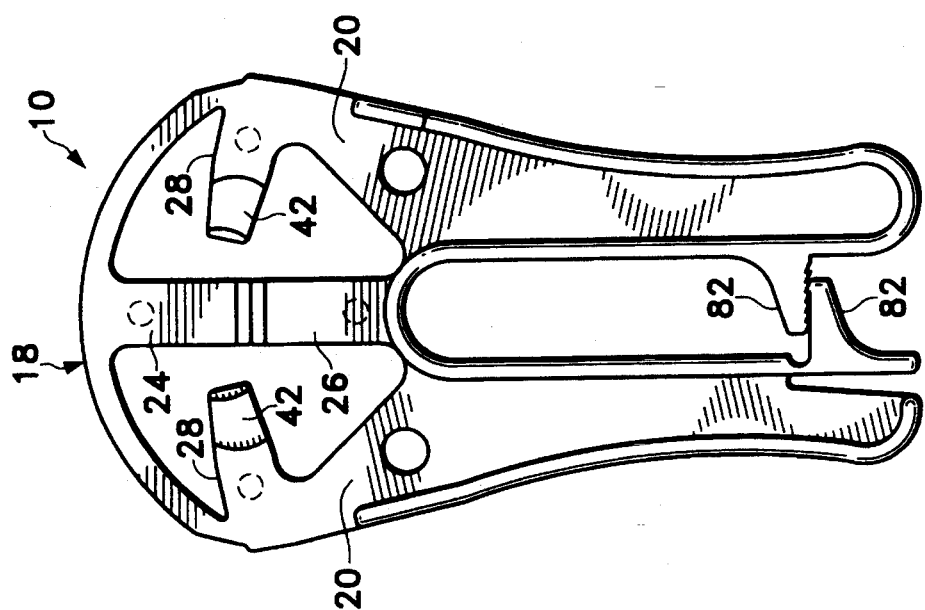
FIG. 8 is a top plan view of the second embodiment of the intraocular lens folder of the present invention similar to FIG. 6 but illustrating the folder in its flexed, deformed and locked state.

As best seen in FIGS. 6, 7 and 8, folder 10 may alternatively contain clasp 82 that holds folder 10 with rim 18 in a flattened state until clasp 82 is disengaged.

This description is given for purposes of illustration and explanation. It will be apparent to those skilled in the art that modifications and changes may be made to the invention described herein without departing from its scope or spirit.

We claim:

1. An intraocular lens folder, comprising:

a) a first handle and a second handle, both handles having upper portions and terminal ends opposite the upper portions;

b) a hinge connecting the first handle to the second handle between the upper portions and the terminal ends;

c) a deformable rim generally arcuate in shape extending between the upper portion of the first handle and the upper portion of the second handle thereby defining a half ring-like head with a hollow center;

d) a first jaw having a first jaw face projecting into the hollow center from the rim;

e) a second jaw having a second jaw face projecting into the hollow center from the hinge generally opposite the first jaw;

f) a slot formed in the first jaw open to the first jaw face; and g) a tab formed in the second jaw on the second jaw face that is received in the slot as the first jaw face and the second jaw face are forced together.

2. The intraocular lens folder of claim 1 further comprising a third jaw and a fourth jaw, both jaws having recesses and projecting into the hollow center from the upper portions of the first handle and the second handle, respectively.

3. The intraocular lens folder of claim 1 wherein the folder comprises plastic.

4. An intraocular lens folder, comprising:

a) a first handle and a second handle, both handles having upper portions and terminal ends opposite the upper portions;

b) a hinge connecting the first handle to the second handle between the upper portions and the terminal ends;

c) a deformable rim generally arcuate in shape extending between the upper portion of the first handle and the upper portion of the second handle thereby defining a half ting-like head with a hollow center;

d) a first jaw projecting into the center from the rim;

e) a second jaw projecting into the center from the rim; and f) a means for holding the rim in a flattened state.

5. The intraocular lens folder of claim 4 wherein the folder comprises plastic.

6. The intraocular lens folder of claim 4 wherein the first jaw and the second jaw have jaw faces, the jaw face of the second jaw having a tab that fits into a slot in the jaw face of the first jaw as the first jaw face and the second jaw face are forced together.

7. The intraocular lens folder of claim 4 wherein the means for holding the rim in a flattened state comprises a clasp affixed to the handles.

8. An intraocular lens folder, comprising:

a) a first handle and a second handle, both handles having upper portions and terminal ends opposite the upper portions;

b) a hinge connecting the first handle to the second handle between the upper portions and the terminal ends;

c) a deformable rim generally arcuate in shape extending between the upper portion of the first handle and the upper portion of the second handle thereby defining a half ting-like head with a hollow center;

d) a first jaw projecting into the hollow center from the rim having a jaw face with a tab;

e) a second jaw projecting into the hollow center from the hinge generally opposite the first jaw having a jaw face with a slot that aligns with the tab on the first jaw face;

f) a third jaw having a recess and projecting into the hollow center from the upper portion of the first handle;

g) a fourth jaw having a recess and projecting into the hollow center from the upper portion of the second handle generally opposite the third jaw; and h) a clasp affixed to the handles.

9. The intraocular lens folder of claim 8 wherein the folder comprises plastic.

* * * * *